(12) United States Patent
Nickel et al.

(10) Patent No.: US 7,624,648 B2
(45) Date of Patent: Dec. 1, 2009

(54) SYSTEM AND METHOD FOR MULTI-AXES SIMULATION

(75) Inventors: Troy D. Nickel, Minneapolis, MN (US); David J Deviley, Apple Valley, MN (US)

(73) Assignee: Bose Corporation, Framingham, MA (US)

(*) Notice: Subject to any disclaimer, the term of this patent is extended or adjusted under 35 U.S.C. 154(b) by 36 days.

(21) Appl. No.: 11/768,675

(22) Filed: Jun. 26, 2007

(65) Prior Publication Data
US 2009/0000388 A1   Jan. 1, 2009

(51) Int. Cl.
*G01N 3/00* (2006.01)
(52) U.S. Cl. .................................................. 73/856
(58) Field of Classification Search .............. 73/789, 73/794, 798, 812
See application file for complete search history.

(56) References Cited

U.S. PATENT DOCUMENTS

| | | | | |
|---|---|---|---|---|
| 3,793,880 | A * | 2/1974 | Sugi et al. ................. | 73/797 |
| 4,607,531 | A * | 8/1986 | Meline et al. ............. | 73/794 |
| 4,748,854 | A * | 6/1988 | Rao ............................ | 73/799 |
| 4,802,365 | A * | 2/1989 | Sallberg et al. ............ | 73/808 |
| 4,869,111 | A * | 9/1989 | Ohya et al. ................. | 73/811 |
| 5,291,279 | A * | 3/1994 | Imao ........................... | 348/92 |
| 5,952,581 | A * | 9/1999 | Lammers et al. .......... | 73/831 |
| 6,035,715 | A * | 3/2000 | Porter ......................... | 73/571 |
| 6,247,366 | B1 * | 6/2001 | Porter ......................... | 73/571 |
| 6,550,323 | B1 * | 4/2003 | Nguyen et al. ............ | 73/158 |
| 6,718,833 | B2 * | 4/2004 | Xie et al. .................... | 73/812 |
| 7,201,061 | B2 * | 4/2007 | Hurd et al. ................. | 73/791 |
| 7,204,152 | B2 * | 4/2007 | Woodward et al. ........ | 73/794 |
| 7,204,153 | B2 * | 4/2007 | Phipps ........................ | 73/808 |
| 7,254,995 | B2 * | 8/2007 | Leska et al. ................ | 73/146 |
| 2002/0162400 | A1 * | 11/2002 | Xie et al. .................... | 73/812 |
| 2006/0243042 | A1 * | 11/2006 | Leska et al. ................ | 73/146 |
| 2007/0068274 | A1 | 3/2007 | Olson et al. | |

FOREIGN PATENT DOCUMENTS

EP    1598655    3/2008

OTHER PUBLICATIONS

International Search Report and Written Opinion dated Mar. 4, 2009 for International Application No. PCT/US2008/068285.
International Preliminary Report on Patentability dated Jul. 9, 2009 for PCT/US2008/068285.

* cited by examiner

*Primary Examiner*—Lisa M Caputo
*Assistant Examiner*—Freddie Kirkland, III (57) ABSTRACT

A multi-axis fatigue testing device includes a multiple input, multiple output mechanical linkage driven by a plurality of actuators and a controller operating each of the plurality of actuators in real time and in synchronization to produce user-defined multiple fatigue cycle profiles.

9 Claims, 10 Drawing Sheets

SYSTEM AND METHOD FOR MULTI-AXES SIMULATION

BACKGROUND

This disclosure relates to testing devices and methods for medical implant devices.

SUMMARY

A multi-axis fatigue testing device includes a multiple input, multiple output mechanical linkage driven by a plurality of actuators and a controller operating each of the plurality of actuators in real time and in synchronization to produce user-defined multiple fatigue cycle profiles.

One embodiment of the present invention is directed to a multi-axis fatigue device comprising: a sample holder configured to hold a test member; a multiple input, multiple output linkage acting on the sample holder to cause deformation of the sample holder in a plurality of axes; a plurality of actuators driving the multiple input multiple output linkage; and a controller operating each of the plurality of actuators to produce a user-specified cycle profile for each of the plurality of axes. In one aspect, one of the plurality of axes represents a bend angle. In one aspect, one of the plurality of axes represents an axial strain. In one aspect, one of the plurality of axes represents an axial strain and another of the plurality of axes represents a bend angle. In one aspect, one of the plurality of axes represents a torsion. In one aspect, one of the plurality of axes represents a hoop strain. In one aspect, the controller is configured to permit a user to select a cycle profile for one or more of the plurality of axes. In one aspect, the user-specified cycle profile for each of the plurality of axes simulates an expected in-use condition of an implanted test member. In one aspect, the user-specified cycle profile is non-sinusoidal. In one aspect, a first cycle profile for a first axis of the plurality of axes differs from a second cycle profile for a second axis of the plurality of axes by a phase angle. In one aspect, the controller is configured to permit the user to select a second cycle profile for each of the plurality of axes, the second cycle profile for each of the plurality of axes simulates a second expected in-use condition of the implanted test member. In one aspect, the test member comprises a stent. In one aspect the linkage comprises a four-bar linkage. One aspect further comprises a plurality of sample holders, each configured to hold a test member. In one aspect, the multiple input, multiple output linkage acts on each of the plurality of sample holder to cause deformation of each of the plurality of sample holders in the plurality of axes.

Another embodiment of the present invention is directed to a multi-axis fatigue device comprising: a sample holder; a first actuator causing deformation of the sample holder along at least a first deformation axis; a second actuator causing deformation of the sample holder along at least a second deformation axis; and a controller operating the first and second actuators to produce a first cycle profile associated with the first deformation axis and a second cycle profile associated with the second deformation axis, wherein a deformation along the first deformation axis is determined by the first and second actuator. One aspect further comprises a mechanical linkage coupled to the first and second actuators, the mechanical linkage, in response to the first and second actuators causing a deformation of the sample holder along the first and second deformation axes. In one aspect, the first deformation axis represents a bend angle. In one aspect, the first deformation axis represents an axial strain. In one aspect, the second deformation axis represents a bend angle. In one aspect, the controller is configured to permit a user to select a cycle profile for one or more of the deformation axes. In one aspect, the user-specified cycle profile for each of the first and second deformation axes simulates an expected in-use condition of an implanted test member. In one aspect, the user-specified cycle profile is non-sinusoidal. In one aspect, a first cycle profile for the first deformation axis differs from a second cycle profile for the second deformation axis by a phase angle. In one aspect, the controller is configured to permit the user to select a second cycle profile for each of the first and second deformation axis, the second cycle profile for each of the first and second deformation of axis simulates a second expected in-use condition of the implanted test member. In one aspect, the implanted test member comprises a stent. In one aspect, the mechanical linkage comprises a four-bar linkage. One aspect further comprises a plurality of sample holders, each configured to hold a test member.

Another embodiment of the present invention is directed to a method comprising: receiving a set of test parameter data; calculating a first set of positions for a first actuator based on at least a portion of the set of test parameter data, the first set of positions defining a state of the first actuator over a fatigue cycle; calculating a second set of positions for a second actuator based on at least a portion of the first set of positions for the first actuator, the second set of positions defining a state of the second actuator over the fatigue cycle; and repeatedly operating the first actuator according to the calculated first set of positions and the second actuator according to the calculated second set of positions for a predetermined number of cycles, wherein operation of the first actuator and second actuator produces deformation of a test member along a first deformation axis according to a first cycle profile and along a second deformation axis according to a second cycle profile. In one aspect, the first cycle profile is non-sinusoidal. One aspect further comprises calculating a third set of positions for a third actuator based on at least a portion of the set of test parameter data, the third set of positions defining a state of the third actuator over a fatigue cycle; and repeatedly operating the third actuator according to the calculated third set of positions for a predetermined number of cycles, wherein operation of the third actuator produces deformation of the test member along a third deformation axis according to a third cycle profile. In one aspect, the third cycle profile represents a torsional deformation. One aspect further comprises calculating a fourth set of positions for a fourth actuator based on at least a portion of the set of test parameter data, the fourth set of positions defining a state of the fourth actuator over a fatigue cycle; and repeatedly operating the fourth actuator according to the calculated fourth set of positions for a predetermined number of cycles, wherein operation of the fourth actuator produces deformation of the test member along a fourth deformation axis according to a fourth cycle profile. In one aspect, the fourth cycle profile represents a hoop deformation.

BRIEF DESCRIPTION OF THE DRAWINGS

FIG. 5b illustrates a state path followed by the first and second actuators for the fatigue cycle shown in FIG. 5a.

DETAILED DESCRIPTION

Figure 1A:
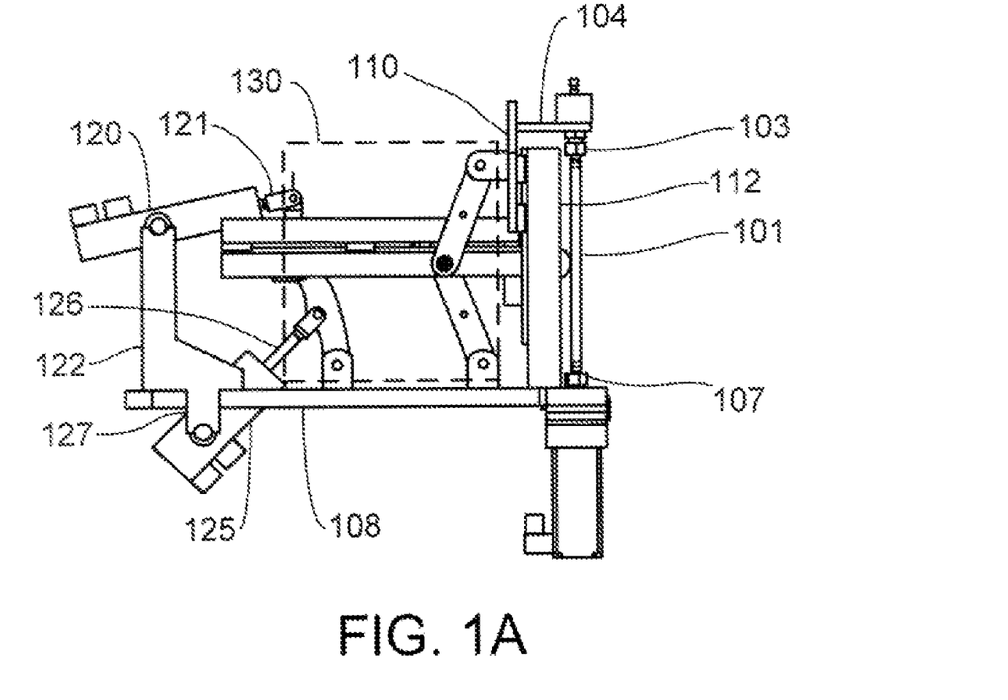
FIG. 1a is side view of a multi-axis fatigue testing device.
Figure 1B:
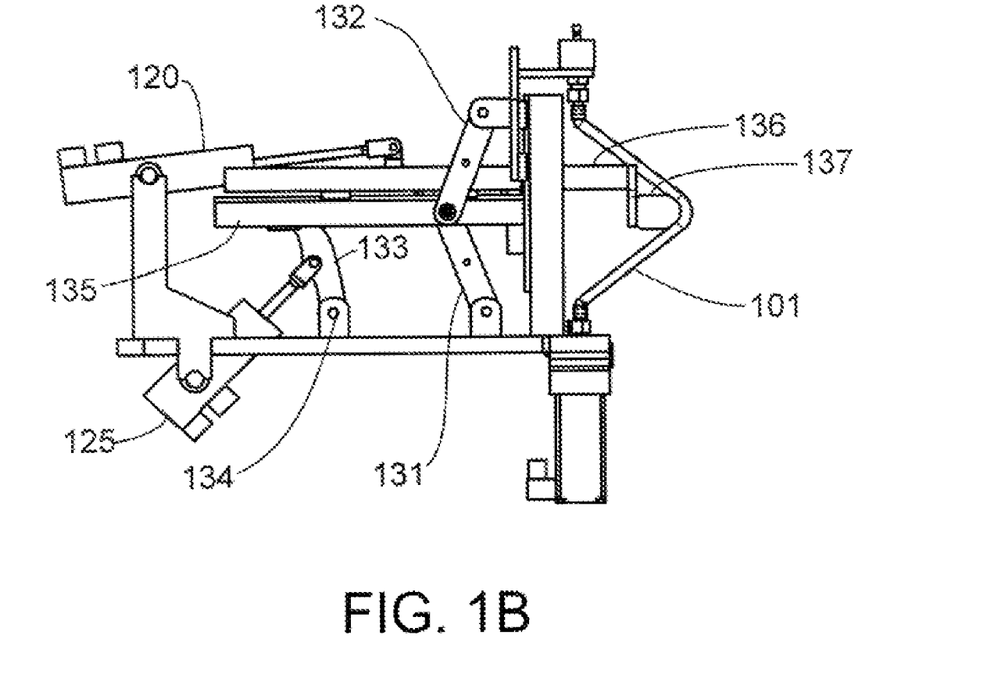
FIG. 1b is a side view of the fatigue testing device shown in FIG. 1a at a different point in a fatigue cycle.

FIGS. 1a and 1b are a side view of a multi-axis fatigue testing device at two instants in a fatigue cycle. In FIGS. 1a and 1b, a test member such as an implantable stent is held within a sample holder 101, which acts as the target tubular vessel for the stent. The upper and lower ends of the sample holder are attached to an upper grip 103 and lower grip 107, respectively. The upper and lower grips, also referred to as fittings, provide fluid communication between an external fluid circuit, not shown, and the lumen of the sample holder. The external fluid circuit may provide both a mean flow and a pulsatile flow through the sample holder thereby simulating conditions in, for example, an artery. Although the side views of FIGS. 1a and 1b do not show multiple sample holders, it should be understood that additional sample holders located behind the sample holder 101 shown in FIG. 1a may be driven by the multi-axis fatigue device.

The lower grip is supported by a lower stage 108. In some embodiments, the lower grip may rotate around the longitudinal axis of the sample holder to apply a torsion or twist to the sample during fatigue testing. The upper grip is supported by an upper stage 104. In some embodiments, the upper grip may rotate around the longitudinal axis of the sample holder to apply a torsion to the sample during fatigue testing. The upper stage is supported by an upper stage support 110, which is slidably attached to a vertical slide support 112 that allows the upper stage to translate vertically relative to the lower stage.

Movement of the upper stage support is controlled by a second actuator 125 through a mechanical linkage 130. In the example illustrated in FIG. 1, the mechanical linkage is a four-bar linkage but other types of mechanical linkages may be used. The four-bar linkage includes a first link 131 pivotally supported at one end by a mezzanine stage 135 and pivotally anchored at the other end to the upper stage support 110. A second link 133 is pivotally supported at one end by the lower stage 108 and pivotally supported at the other end by the mezzanine stage 135. In the example shown in FIG. 1, the lengths of the first and second links and the effective pin-to-pin distances of the mezzanine stage and the lower stage are the same. The four-bar link configuration shown in FIG. 1a effectively guides the mezzanine stage parallel to the lower stage in all positions of the second (input) link 133. A third link 132 is pivotally supported at one end by the lower stage 108 and pivotally supported at the other end by the mezzanine stage 135. In the example shown in FIGS. 1a and 1b, the third link 132 is the same length as the first link 131, effectively driving the upper stage 104 twice the distance of the mezzanine stage.

A bend tool support 136 is slidably supported by the mezzanine stage 135. A bend tool assembly 137 is attached to one end of the bend tool support 138. The other end of the bend tool support 138 is pivotally attached to the drive shaft 121 of the first actuator 120. The first actuator 120 is pivotally supported by a first actuator support 122 attached to the lower stage 108. The second actuator 125 is pivotally supported by a second actuator support 127 attached to the lower stage 108. The drive shaft 126 of the second actuator 126 is pivotally attached to the second link 133 at a point midway between the lower stage pivot axis 134 and the mezzanine stage pivot axis (not shown) of the second link 133.

In the fatigue cycle illustrated in FIGS. 1a and 1b, the second actuator 125 is held stationary during the fatigue cycle and only the first actuator 120 drives the bend tool support 138 horizontally to bend and stretch sample holder 101. In this configuration, the bend angles and axial strains imparted on the sample holder throughout the fatigue cycle are constrained by geometry and cannot be varied independently. Simulation of in-use conditions, however, generally requires independently selectable maximum bend angle and maximum axial strain of the tested stent. In the configuration shown in FIGS. 1a and 1b, the bend angle depends on the drive shaft positions of both the first and second actuators. Similarly, the axial strain depends on the drive shaft positions of both the first and second actuators. A change in the drive shaft position of one of the actuators affects both the bend angle and axial strain of the sample holder. A change in one actuator to cause a desired bend angle, for example, may cause an undesired change in axial strain. In order to effect a desired bend angle and axial strain on the sample holder, neither actuator can be operated independently of the other actuator. When, for example, the maximum bend angle and maximum axial strain are independently selected by the user, the control of the first actuator 120 and second actuator 125 should be synchronized.

As used herein, multi-axis refers to deformation of the sample holder and the stent in more than one axis. In the example shown in FIG. 1, bending of the sample holder is deformation along a first test axis and axial elongation is deformation of the sample holder along a second test axis. If the upper and lower grips are rotated during a fatigue cycle, the torsion applied to the sample holder and stent would represent a deformation of the sample holder along a third test axis. Similarly, when the external circuit applies a pulsatile flow to the lumen of the sample holder, the resulting hoop strain would represent a deformation of the sample holder along a fourth test axis. Each test axis has an associated deformation cycle profile also referred to as a cycle profile that describes the deformation along the associated test axis during each fatigue cycle. During a fatigue test, each a plurality of cycle profiles may be used for each test axis. For example, a user may wish to simulate both walking and climbing stairs in a fatigue test. In such a situation, a first set of cycle profiles may be used to simulate walking and a second set of cycle profiles may be used to simulate stair climbing.

Figure 2:
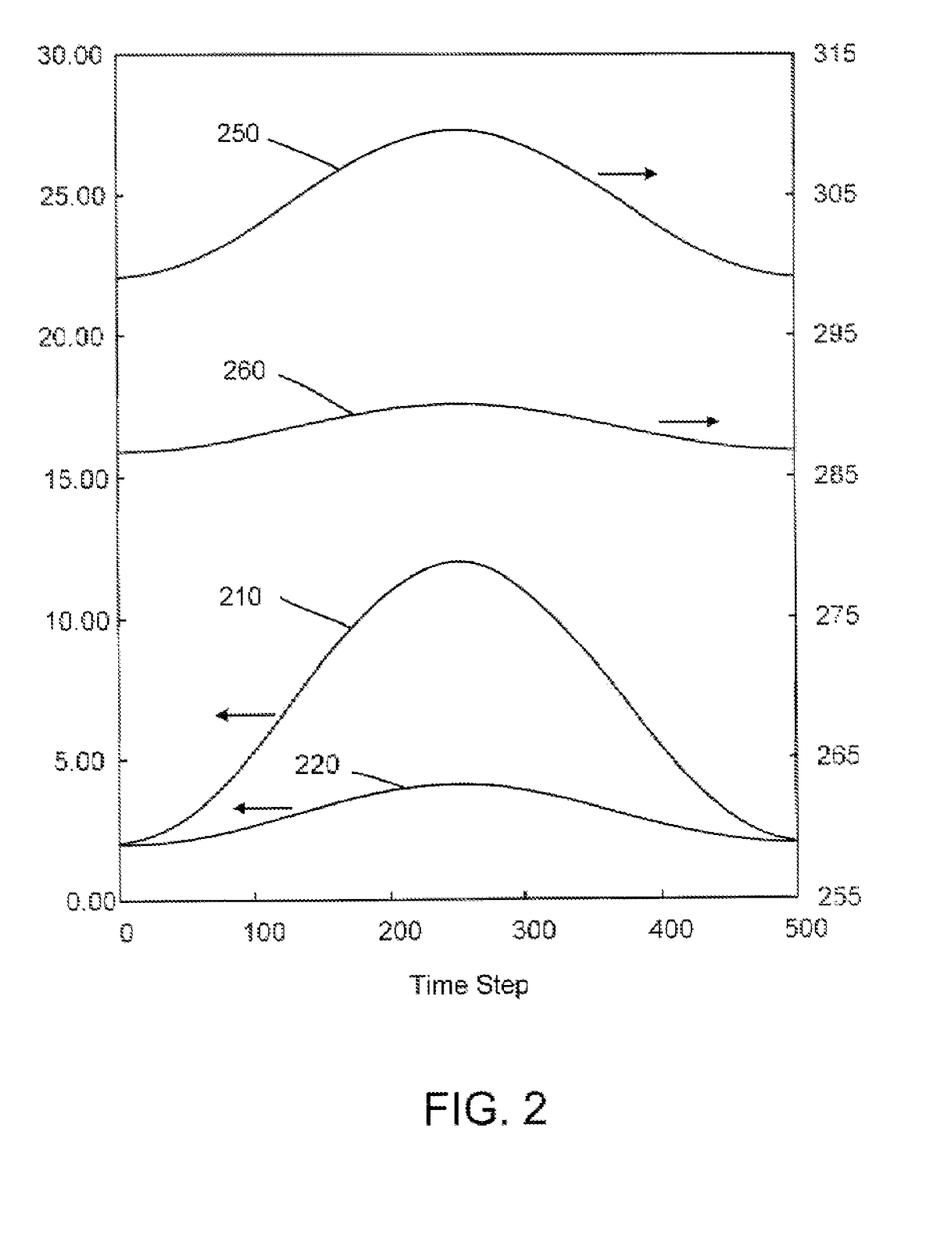
FIG. 2 Illustrates an example of a bend angle and axial strain cycle profiles and displacements of first and second actuators in the embodiment shown in FIG. 1.

FIG. 2 Illustrates the displacements of the first and second actuator and a bend angle cycle profile and an axial strain cycle profile over one fatigue cycle. In FIG. 2, the axial strain of the sample is indicated by line 210, the sample bend angle is indicated by line 220, the displacement of the first actuator is indicated by line 260 and the displacement of the second actuator is indicated by line 250. The axial strain begins at 2% and rises to a maximum axial strain of 12%. The beginning bend angle is set at 2° and increases to a maximum bend angle of 4°. The beginning axial strain, maximum axial strain, beginning bend angle, and maximum bend angle are independently selected by the user, preferably via a computer program interface. FIG. 2 illustrates a sinusoidal cycle profile for both the axial strain and bend angle but if is understood that embodiments of the present invention are not limited to sinusoidal cycle profiles. In some embodiments, the user may select a cycle profile from a set of pre-selected cycle profiles or may input a desired cycle profile for the bend angle and a second desired cycle profile for the axial strain. After the desired cycle profiles are selected or entered by the user, a control program calculates the desired extensions of the drive shafts of the first and second actuators during the fatigue cycle.

Figure 3:
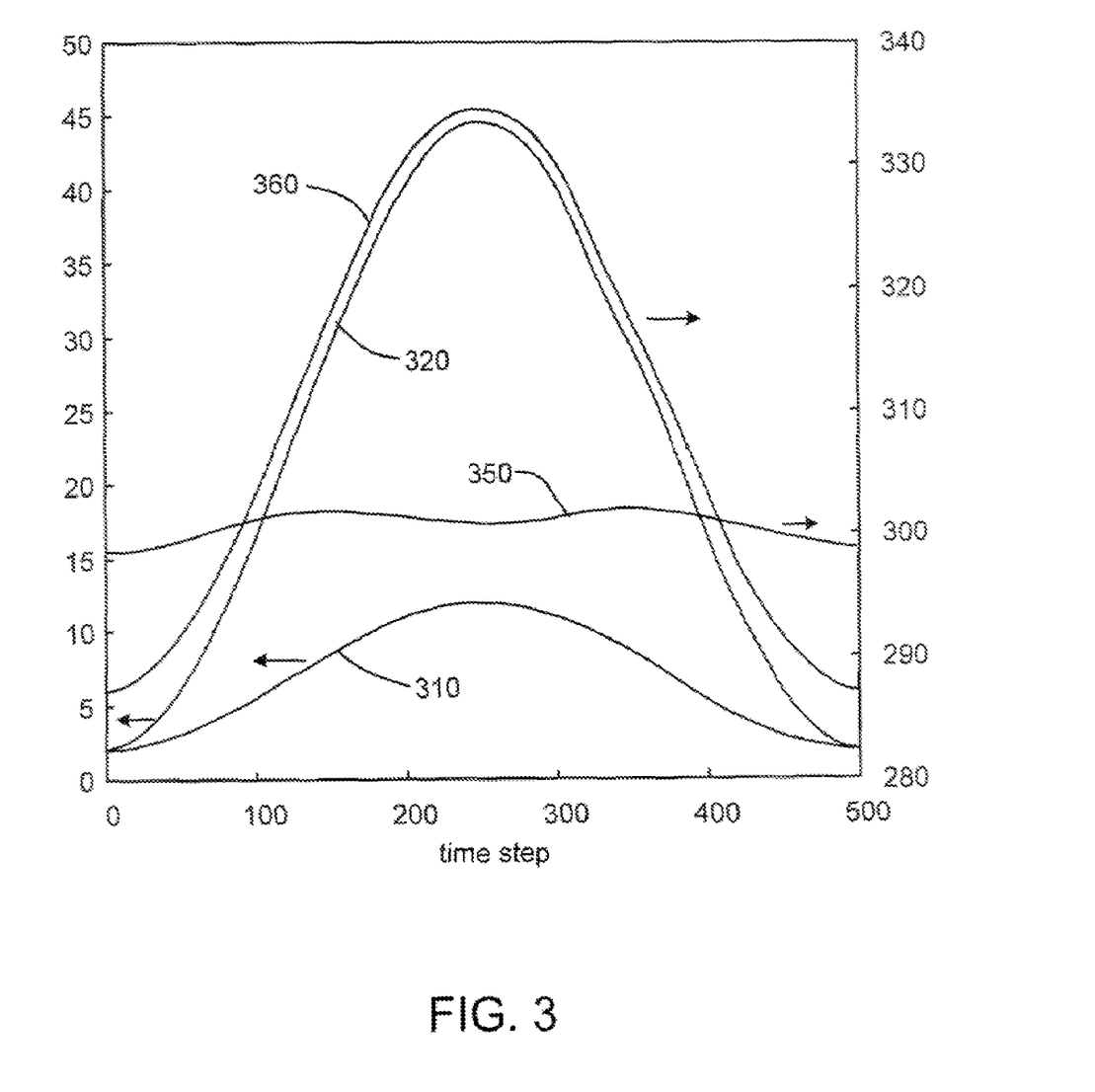
FIG. 3 illustrates an example of a different bend angle and axial strain cycle profiles and the displacements of the first and second actuators in the embodiment shown in FIG. 1.

FIG. 3 Illustrates the displacements of the first and second actuator and the sample bend angle and axial strain over one fatigue cycle having a different maximum bend angle from the one shown in FIG. 2. In FIG. 3, the axial strain of the sample is indicated by line 310, the sample bend angle is indicated by line 320, the displacement of the first actuator is indicated by line 360 and the displacement of the second actuator is indicated by line 350. In FIG. 3, the axial strain begins at 2% and rises to a maximum axial strain of 12% and the beginning bend angle is set at 2° and increases to a maximum bend angle of 47°.

Figure 4:
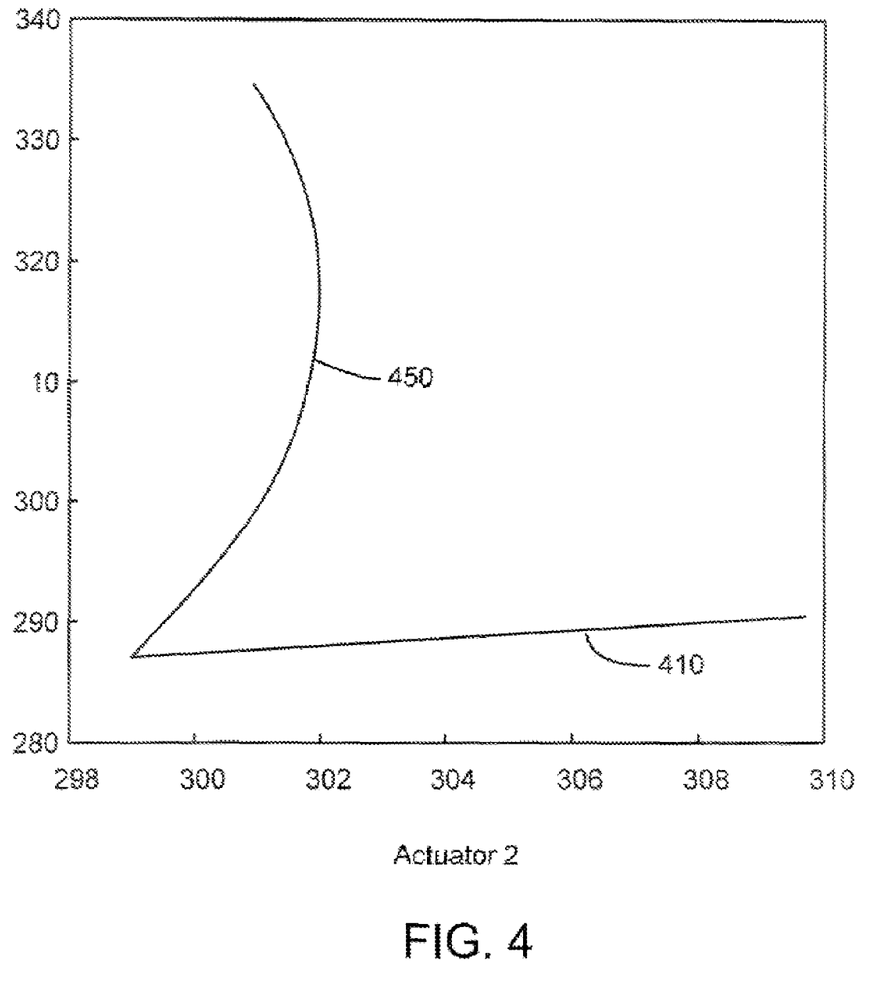
FIG. 4 illustrates a state path followed by the first and second actuators for the fatigue cycles shown in FIGS. 2 and 3.

FIG. 4 displays the actuator state path followed by the first and second actuators for the fatigue cycles shown in FIGS. 2 and 3. In FIG. 4, the extension of the first actuator is shown along the y-axis and the extension of the second actuator is shown along the x-axis. The curve associated with reference 410 illustrates a state of the first and second actuators required to produce the bend and strain fatigue cycle shown in FIG. 2. The curve associated with reference 450 illustrates a state of the first and second actuators required to produce the bend and strain fatigue cycle shown in FIG. 3. Neither of the curves shown in FIG. 4 is linear, which would be the expected path when both actuators mimic the sinusoidal profile of the desired bend and strain cycle profiles shown in FIGS. 2 and 3.

Figure 5A:
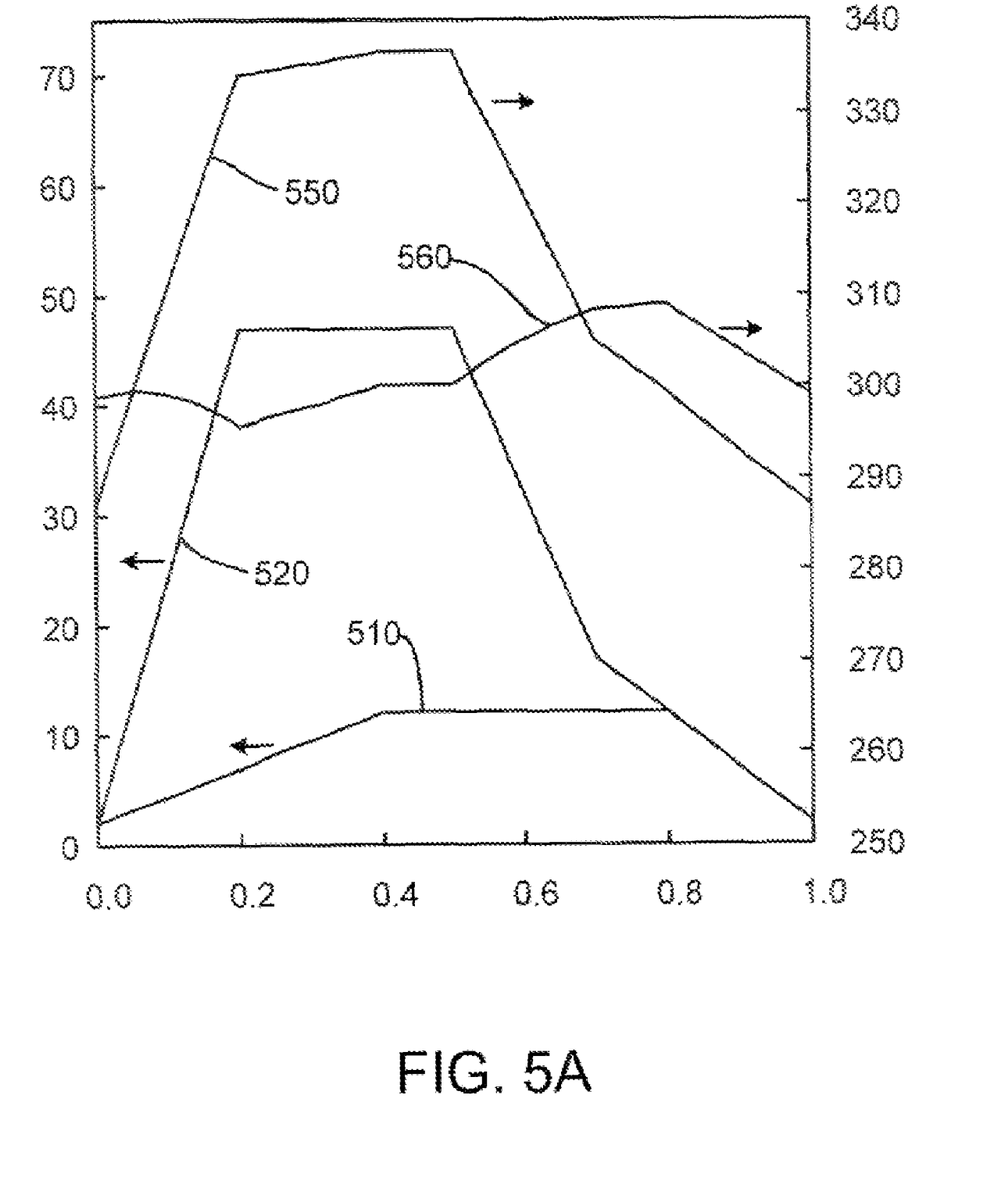
FIG. 5a illustrates an example of a user-defined bend angle and axial strain cycle profiles and the displacements of the first and second actuators in the embodiment shown in FIG. 1.
Figure 5B:
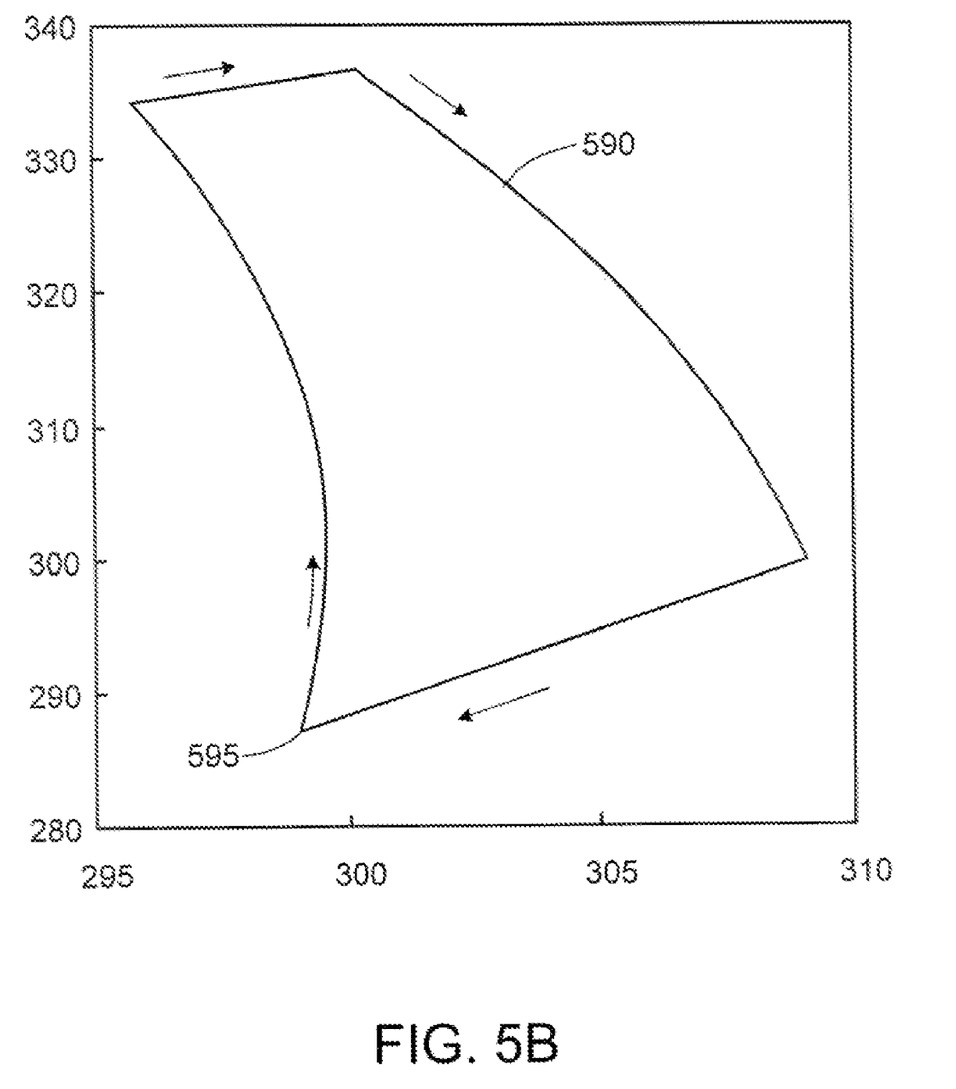

FIG. 5a illustrates a user-defined bend angle cycle profile 520 and axial strain cycle profile 510 and the resulting displacements of the first actuator 550 and the second actuator 560 over one fatigue cycle. The user-defined bend angle and axial strain cycle profiles shown in FIG. 5a illustrates that the bend angle and axial strain are not limited to sinusoidal shapes and each can be any arbitrary shape. The capability of enabling entry of user-defined arbitrary bend angle and axial strain fatigue cycle shapes allows the user to more closely simulate the often complicated bending and stretching that the stent is likely to experience when implanted into its target vessel. FIG. 5b displays the actuator state path followed by the first and second actuators for the fatigue shown in FIG. 5a. The start of the fatigue cycle is indicated by point 595 and the arrows indicate the direction of time around the closed state path 590.

Figure 6:
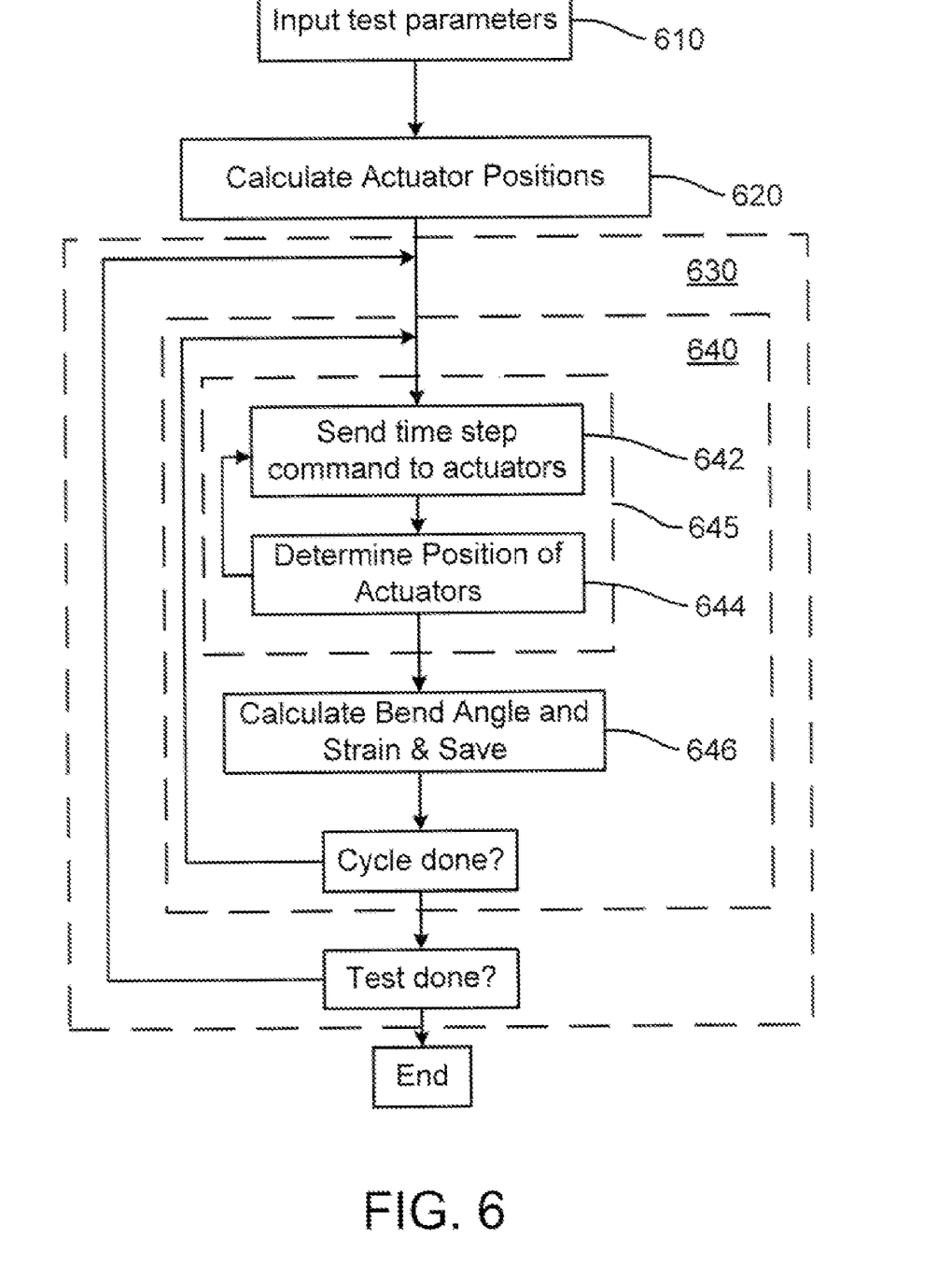
FIG. 6 is a diagram illustrating operation of a multi-axis fatigue testing device.

FIG. 6 is a flow diagram illustrating a process for performing a fatigue test. A user begins a fatigue test by entering a set of test parameter data at step 810. The test parameter set includes information such as number of fatigue cycles, initial bend angle, maximum bend angle, initial axial strain, maximum axial strain, sample tube diameter, and bend tool radius. If the test includes applying a torsion and/or pulsatile extension, information defining these profiles are entered by the user. The user may also enter an axial strain profile and/or a bend profile that simulates the expected in-use profile more closely than a default profile such as a sinusoidal profile. User data entry of test parameters is preferably through a user interface provided as part of a software/hardware testing platform for mechanical testing machines. Such a platform may include a computer executing a control program and control electronics that interface the test machine's actuators and measurement transducers to the control program. The control program includes a user interface for entering test parameters and viewing test conditions and results, a module for controlling the control electronics, and a module for receiving and converting signals from the testing machine's actuators and transducers into test data and saving the test data to a computer readable media. An example of such a platform is the WinTest® PCI Controls platform available from the Electro-Force Systems Group of Bose Corporation of Eden Prairie, Minn.

Actuator positions at each time step in a fatigue cycle are calculated at step 820 based on the user-entered test parameters and linkage geometry parameters that characterize the mechanical linkage of the testing device. The linkage geometry parameters may be stored on computer readable memory that does not require user entry. In some modular testing machines, where different sets of mechanical linkage and actuators may be used, the linkage geometry parameters may be stored in an electronic library that may be retrieved by the testing platform software depending on the mechanical linkage deployed on the modular testing machine. The fatigue cycle is partitioned into a plurality of time steps and a desired position for each actuator is calculated, using at least some of the retrieved geometry parameters, the user entered testing parameters, and the actuator positions at the previous time step. The desired actuator positions may be stored for retrieval during the fatigue testing. The number of time steps in a fatigue cycle maybe determined by balancing the desired smoothness of the actuator control against the increased burden on the computer processor and supporting control modules.

The fatigue test control program includes an outer fatigue loop 630 and a nested inner cycle loop 640 and is preferably executed in real time. The outer fatigue loop 630 is repeated for a user-specified number of fatigue cycles. The inner cycle loop 640 is repeated for a predetermined number of time steps. Within the cycle loop, the desired actuator positions for the current time step are retrieved from memory and are sent to their respective actuators at step 642. Within each actuator, a position sensor measures the current position of the drive shaft of the actuator at step 644 and an internal control loop 645, such as a PSD loop, using the desired position and the actual position drives the actuator toward the desired position. The current position of each actuator is used to calculate the current bend angle and axial strain of the sample and that information is stored onto computer readable media in real time.

It should be understood that the mechanical linkage shown in FIG. 1 is an illustrative example that is not meant to be limiting. The linkage shown in FIG. 1 is an example of a Multiple-Input-Multiple-Output (MIMO) linkage where the linkage is driven by more than one actuator that effects a change in more than one test axis such as bend angle and axial strain. In order to independently control the output variables, the actuators cannot be independently controlled but must be driven in a coordinated way to produce the independently selected output cycle profiles.

Figure 7:
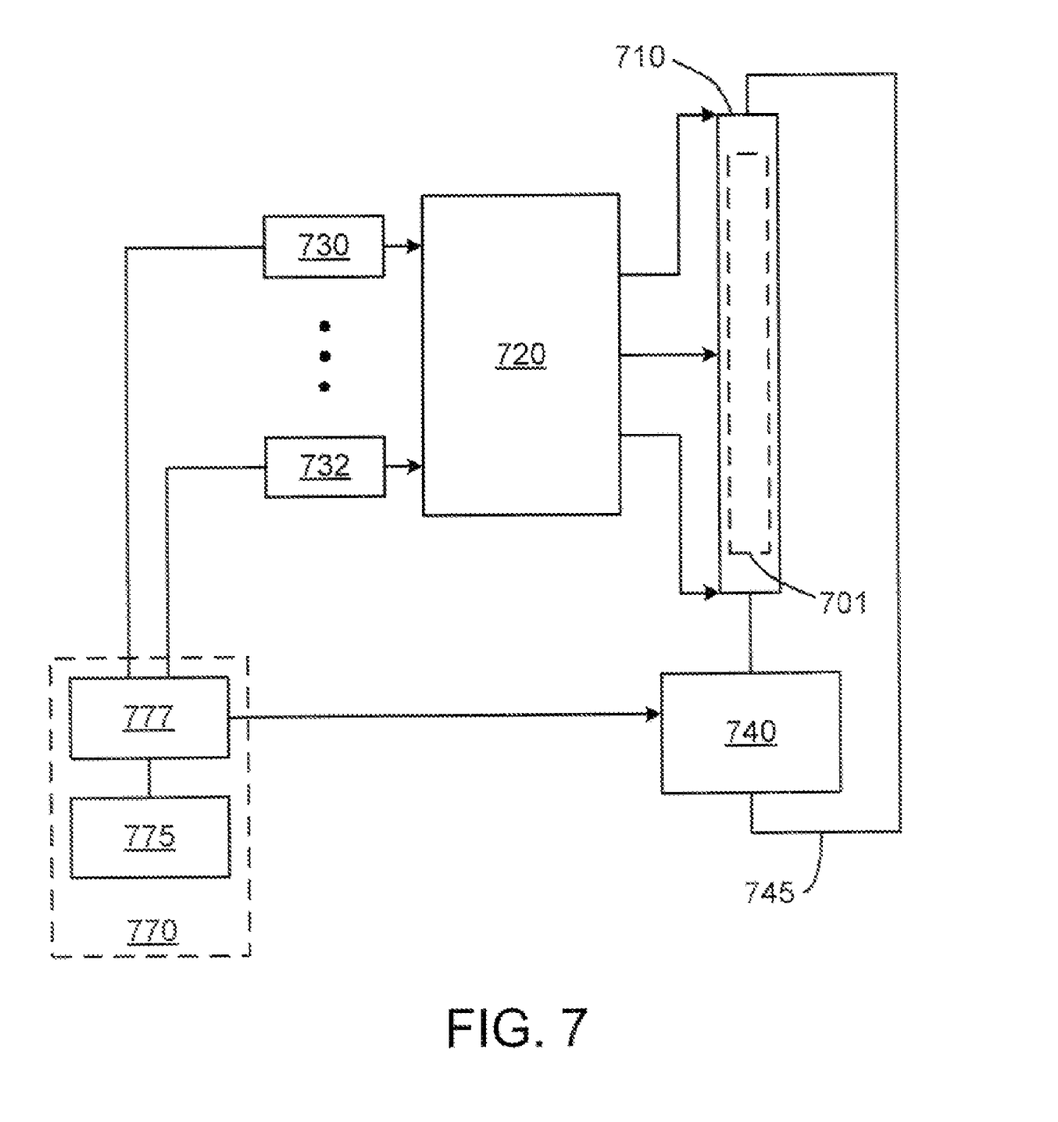
FIG. 7 is a block diagram illustrating a multi-axis fatigue testing device.

FIG. 7 is a block diagram illustrating an embodiment of the present invention. in FIG. 7, a multiple input, multiple output (MIMO) linkage 720 deforms a sample holder 710 holding a stent 701 according to one or more user-defined deformation cycle profiles. MIMO linkage 720 is driven by a plurality of actuators 730, 732. A controller 770 operates or controls actuators 730, 732 to produce the desired deformation in the sample holder 710. The lumen of the sample holder 710 is in fluid communication with an external flow circuit 745. The external flow circuit includes at least one fluid moving device 740 such as a pump or bellows that moves the fluid through the lumen of the sample holder 710. The fluid moving device 740 is controlled by the controller 770 such that a desired flow rate and pressure is maintained within the lumen of the sample holder 710. The desired flow rate may include a mean flow rate and a pulsatile flow rate.

Controller 770 includes a computer 775 and control circuitry 777. The computer 775 executes a control program that automatically manages a fatigue test and records and stores data obtained from a plurality of instrument transducers, not shown. Control circuitry 777 provides an interface between the executing computer program and the actuators and transducers of the fatigue testing device.

Figure 8:
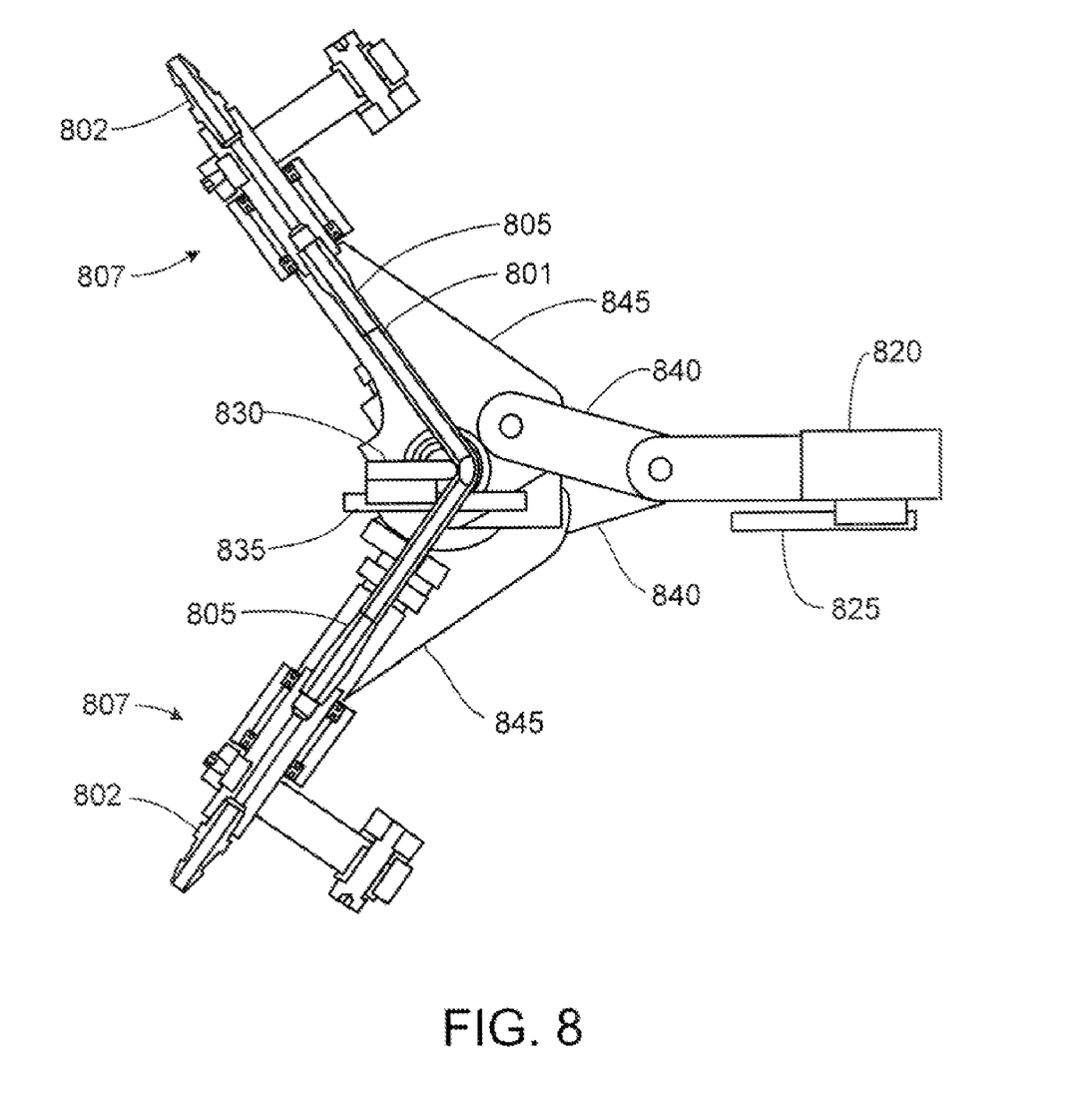
FIG. 8 is a side view of a portion of a multi-axis fatigue testing device.

FIG. 8 is a side sectional view of a portion of a multi-axis fatigue testing device using a MIMO linkage having a configuration different from the configuration shown in FIG. 1. In FIG. 8, sample holder 801 is supported at both ends by grips 805 attached to a torsion assembly 807. Torsion assembly 807 provides the capability to apply torsion to the sample holder 301 during a fatigue cycle. The grips 805 and torsion assemblies 807 provide a flow path to the lumen of the stent held by the sample holder. Flow ports 802 attached to the torsion assembly 807 provide a flow path to an external flow circuit that control the flow and pressure through the lumen of the stent during a fatigue cycle.

Each torsion assembly 807 is supported by a lever arm 845 and rotates around a common pivot axis, not shown. A link 840 is pivotally connected to lever arm 845 at one end of the link and is pivotally connected to a common drive link 820. The common drive link 820 is slidably supported by a drive link support 825. The common drive link 820 is connected to a drive shaft of a first actuator, not shown. A bend tool 830 is slidably supported by bend tool support 835. The bend tool 830 is attached to a second actuator, not shown. The bend tool 830 is positioned and oriented such that the sample holder 801 bends around the bend tool at a midpoint along the sample holder's length.

Figure 9:
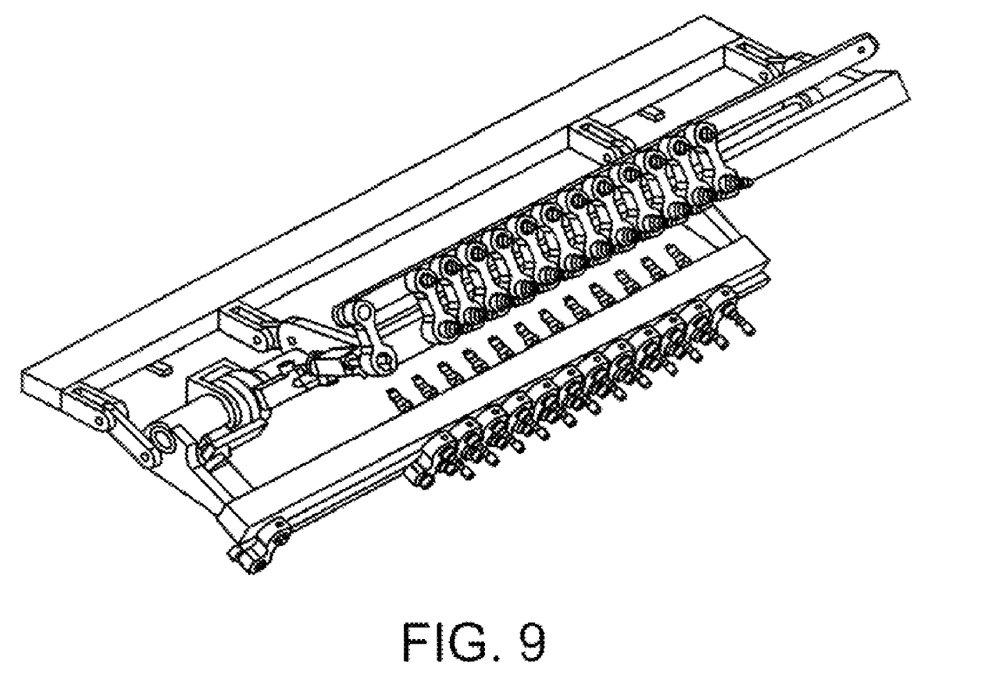
FIG. 9 Is a perspective view of the multi-axis fatigue testing device shown in FIG. 8.

FIG. 9 is a perspective view of the device shown in FIG. 8 and illustrates an example where more than one stent may be tested simultaneously thereby reducing overall testing time while increasing statistical confidence of the results.

Embodiments of the devices described above comprise computer components and computer-implemented steps that will be apparent to those skilled in the art. For example, it should be understood by one of skill in the art that the computer-implemented steps may be stored as computer-executable instructions on a computer-readable medium such as, for example, floppy disks, hard disks, optical disks, Flash ROMS, nonvolatile ROM, and RAM. Furthermore, it should be understood by one of skill in the art that the computer-executable instructions may be executed on a variety of processors such as, for example, microprocessors, digital signal processors, gate arrays, etc. that may be connected to a network and in communication with other processors on the network. For ease of exposition, not every step or element of the devices described above is described herein as part of a computer system, but those skilled in the art will recognize that each step or element may have a corresponding computer system or software component. Such computer system and/or software components are therefore enabled by describing their corresponding steps or elements (that is, their functionality), and are within the scope of the present invention.

Having thus described at least illustrative embodiments of the invention, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed:

1. A multi-axis fatigue device comprising:
a sample holder configured to hold a test member and to act as a target tubular vessel for the test member;
a multiple input, multiple output linkage acting on the sample holder to cause deformation of the sample holder in a plurality of axes;
a plurality of actuators driving the multiple input, multiple output linkage;
a controller operating each of the plurality of actuators to produce a user-specified cycle profile for each of the plurality of axes; and
an external fluid circuit structured to provide fluid flow through the sample holder, wherein the test member comprises a stent.

2. A multi-axis fatigue device comprising:
a plurality of sample holders, each configured to hold a test member;
a multiple input, multiple output linkage acting on the sample holder to cause deformation of the sample holder in a plurality of axes;
a plurality of actuators driving the multiple input, multiple output linkage; and
a controller operating each of the plurality of actuators to produce a user-specified cycle profile for each of the plurality of axes.

3. The device of claim 2 wherein the multiple input, multiple output linkage acts on each of the plurality of sample holder to cause deformation of each of the plurality of sample holders in the plurality of axes.

4. A multi-axis fatigue device comprising:
a sample holder configured to act as a target tubular vessel for an implantable test member;
a first actuator causing deformation of the sample holder along at least a first deformation axis;
a second actuator causing deformation of the sample holder along at least a second deformation axis;
a controller operating the first and second actuators to produce a first cycle profile associated with the first deformation axis and a second cycle profile associated with the second deformation axis, wherein a deformation along the first deformation axis is determined by the first and second actuator, wherein the controller is configured to permit a user to select a cycle profile for one or more deformation axes, and wherein the user-specified cycle profile for each of the first and second deformation axes simulates an expected in-use condition of the implantable test member; and
an external fluid circuit structured to provide fluid flow through the sample holder, wherein the implantable test member comprises a stent.

5. A multi-axis fatigue device comprising:
a plurality of sample holders, each configured to hold a test member;
a first actuator causing deformation of the sample holder along at least a first deformation axis;
a second actuator causing deformation of the sample holder along at least a second deformation axis; and
a controller operating the first and second actuators to produce a first cycle profile associated with the first deformation axis and a second cycle profile associated with the second deformation axis, wherein a deformation along the first deformation axis is determined by the first and second actuator.

6. A method comprising:

receiving a set of test parameter data;

calculating a first set of positions for a first actuator based on at least a portion of the set of test parameter data, the first set of positions defining a state of the first actuator over a fatigue cycle;

calculating a second set of positions for a second actuator based on at least a portion of the first set of positions for the first actuator, the second set of positions defining a state of the second actuator over the fatigue cycle;

calculating a third set of positions for a third actuator based on at least a portion of the set of test parameter data, the third set of positions defining a state of the third actuator over a fatigue cycle;

calculating a fourth set of positions for a fourth actuator based on at least a portion of the set of test parameter data, the fourth set of positions defining a state of the fourth actuator over a fatigue cycle;

repeatedly operating the first actuator according to the calculated first set of positions, the second actuator according to the calculated second set of positions for a predetermined number of cycles, the third actuator according to the calculated third set of positions for a predetermined number of cycles, and the fourth actuator according to the calculated fourth set of positions for a predetermined number of cycles; and wherein operation of the first actuator and second actuator produces deformation of a test member along a first deformation axis according to a first cycle profile and along a second deformation axis according to a second cycle profile, operation of the third actuator produces deformation of the test member along a third deformation axis according to a third cycle profile, and operation of the fourth actuator produces deformation of the test member along a fourth deformation axis according to a fourth cycle profile.

7. The method of claim 6 wherein the first cycle profile is non-sinusoidal.

8. The method of claim 7 wherein the third cycle profile represents a torsional deformation.

9. The method of claim 8 wherein the fourth cycle profile represents a hoop deformation.

* * * * *